United States Patent [19]

Fukui et al.

[11] Patent Number: 4,835,300

[45] Date of Patent: May 30, 1989

[54] FLUORINE CONTAINING URETHANE COMPOUNDS

[75] Inventors: Shosin Fukui, Toyonaka; Masayoshi Shinjo, Settsu; Hirokazu Aoyama, Osaka, all of Japan

[73] Assignee: Daikin Kogyo Co., Ltd., Osaka, Japan

[21] Appl. No.: 925,539

[22] Filed: Oct. 28, 1986

Related U.S. Application Data

[63] Continuation of Ser. No. 581,159, Feb. 17, 1984, abandoned.

[51] Int. Cl.$^4$ ............... C07C 125/073; C07C 125/075
[52] U.S. Cl. ...................................... 560/25; 560/115; 560/158
[58] Field of Search .................... 560/25, 115, 158

[56] References Cited

U.S. PATENT DOCUMENTS 3,398,182  8/1968  Guenther et al. ............... 560/25 X
3,681,426  8/1972  Hahn et al. ....................... 560/25 X

FOREIGN PATENT DOCUMENTS 999795  7/1965  United Kingdom .

*Primary Examiner*—Paul J. Killos
*Assistant Examiner*—Vera C. Clarke
*Attorney, Agent, or Firm*—Armstrong, Nikaido, Marmelstein & Kubovcik

[57] ABSTRACT

A fluorine-containing urethane compounds represented by the formula

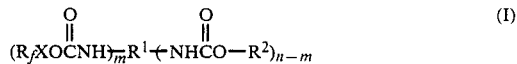

wherein $R_f$ represents a perfluoroalkyl group having 4 to 20 carbon atoms; X represents —CH$_2$CH(A)—, —C$_k$H$_{2k}$— or —SO$_2$N(R$^3$)C$_t$H$_{2t}$— (in which A represents a methyl group or ethyl group; k and t are an integer of 1 to 4; and R$^3$ is hydrogen atom or a lower alkyl group); R$^1$ represents a n-valent organic group; R$^2$ represents an alkyl group having 1 to 5 carbon atoms; n is an integer of 2 to 10; and m is an integer in the range of n≧m≧1, subject to the limitation that when n is 2, m is 2 and R$^1$ is

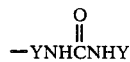

(in which Y is a divalent organic group) and a water and oil-repelling agent and a non-sticking agent containing the compound as the active ingredient.

6 Claims, No Drawings

FLUORINE CONTAINING URETHANE COMPOUNDS

This application is a continuation of application Ser. No. 581,159, filed Feb. 17, 1984, now abandoned.

This invention relates to novel fluorine-containing urethane compounds and particularly to fluorine-containing urethane compounds having as a side chain a perfluoroalkyl group, to water and oil repelling agents containing the above compound as the active ingredient and to non-sticking agents containing the above compound as the active ingredient.

Generally urethane compounds having perfluoroalkyl groups have been known as water and oil repelling agents with good friction resistance and have been put to use as water and oil repelling agents for carpets (U.S. Pat. Nos. 3,896,035 and 3,897,227 and Japanese unexamined patent publication No. 7400/1979). However, the surface of fabrics applied with the conventional fluorine-containing urethane compounds exhibits poor water repellency and the compounds have been unsatisfactory in use as water and oil repelling agents.

We have developed a class of fluorine-containing urethane compounds which are superior to those heretofore known in water and oil repellency and accomplished the present invention.

The fluorine-containing urethane compounds of this invention are represented by the formula (I)

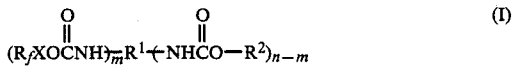
(I)

wherein $R_f$ represents a perfluoroalkyl group having 4 to 20 carbon atoms; X represents $-CH_2CH(A)-$, $-C_kH_{2k}-$ or $-SO_2N(R^3)C_tH_{2t}-$ (in which A represents a methyl group or ethyl group; k and t are an integer of 1 to 4; and $R^3$ is hydrogen atom or a lower alkyl group); $R^1$ represents a n-valent organic group; $R^2$ represents an alkyl group having 1 to 5 carbon atoms; n is an integer of 2 to 10; and m is an integer in the range of $n \geq m \geq 1$, subject to the limitation that when n is 2, m is 2 and $R^1$ is

(in which Y is a divalent organic group). The urethane compounds of the formula (I) are excellent in water and oil repellency and are useful as a material for forming coatings on solid substrates. The present compounds are also useful as non-sticking agents such as mold release agents.

The present compounds of the formula (I) are novel compounds undisclosed in literature and can be easily prepared, for example, by reacting 1 mole of a polyisocyanate of the formula $$R^1-(NCO)_n \qquad (II)$$

wherein n is not 2 with m mole of a fluorine-containing alcohol of the formula $$R_fXOH \qquad (III)$$

to produce a compound of the formula

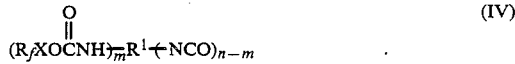

[see Reaction Equation (1) given below] and reacting 1 mole of the compound of the formula (IV) with (n-m) mole of a lower alcohol of the formula $$R^2OH \qquad (V)$$

[see Reaction Equation (2) given below].

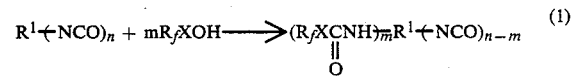

In the above reaction equations, $R_f$, X, $R^1$, $R^2$, m and n are as defined above.

The compounds of the formula (I) wherein m=n=2, namely compounds of the formula (I′)

can be prepared by reacting a diisocyanate compound of the formula OCNYNCO (VI) with a fluorine-containing alcohol of the formula $R_fXOH$ (III) to give a compound of the formula

(see Reaction Equation A given below, and reacting the compound of the formula (VII) with water (see Reaction Equation B given below).

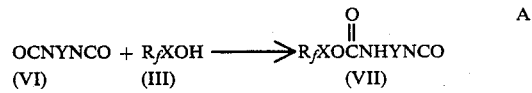

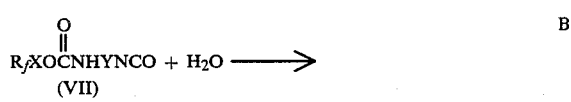

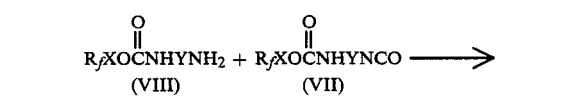

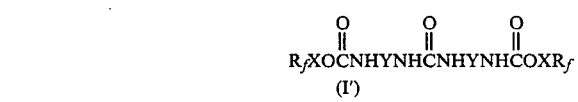

In the above reaction equations, $R_f$, X and Y are as defined above.

Examples of the polyisocyanate compound of the formula (II) useful in Reaction Equation 1 include a broad range of conventional compounds, such as those shown below:

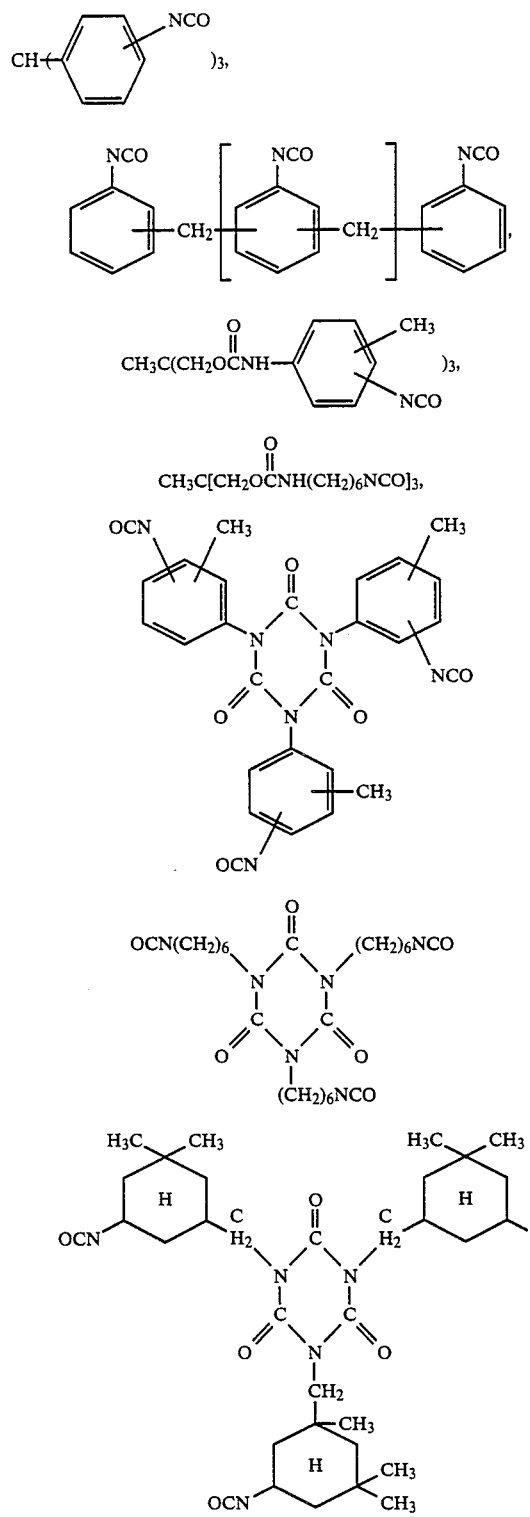

$R^1$ in the formula (II) represents the residual groups excluding the isocyanate of the compounds exemplified above and is a n-valent organic group.

A wide range of conventional compounds can be used as the diisocyanate compound of the formula (VI) to be used in the reaction of Reaction Equation A. Exemplary of such compounds are those indicated below:

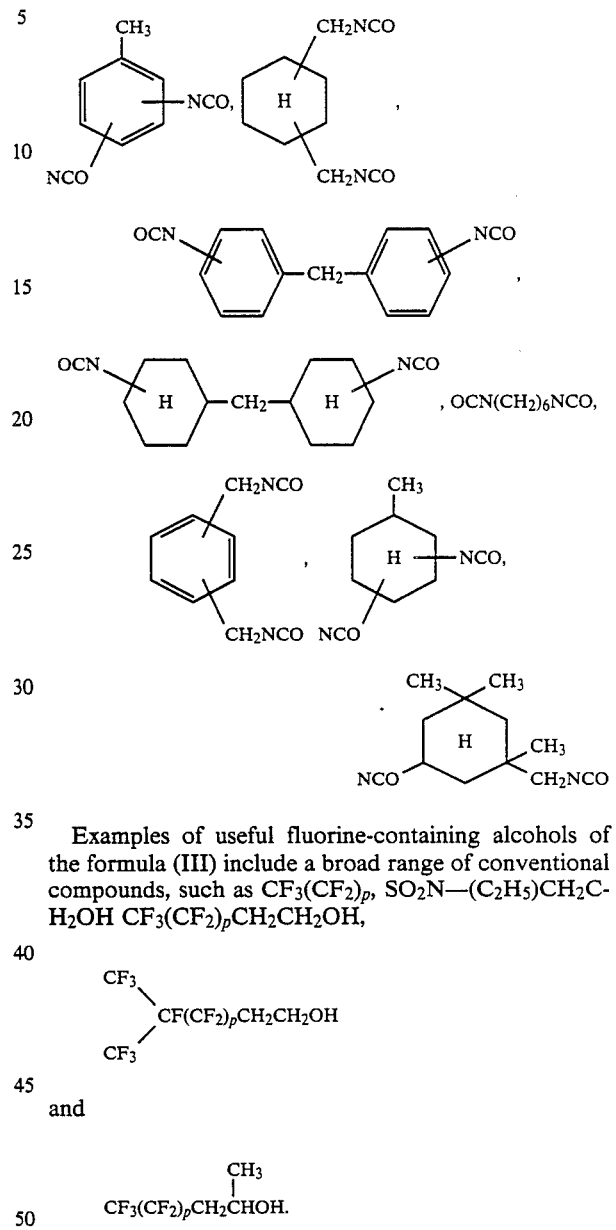

Examples of useful fluorine-containing alcohols of the formula (III) include a broad range of conventional compounds, such as $CF_3(CF_2)_p$, $SO_2N-(C_2H_5)CH_2CH_2OH$ $CF_3(CF_2)_pCH_2CH_2OH$, $$\begin{array}{c}CF_3\\ \phantom{CF_3}\diagdown\\ \phantom{CF_3}\phantom{-}CF(CF_2)_pCH_2CH_2OH\\ \phantom{CF_3}\diagup\\ CF_3\end{array}$$

and $$CF_3(CF_2)_pCH_2\overset{CH_3}{\underset{|}{C}}HOH.$$

In the foregoing formulae, p is an integer of 3 to 10. The perfluoroalkyl group has 4 to 20 carbon atoms, preferably 5 to 16 carbon atoms.

Representative of the lower alcohol groups in the formula (V) are methanol, ethanol, propanol butanol, etc.

The reaction of the polyisocyanate compound (IV) in Reaction Equation (1) or the diisocyanate compound (VI) in Reaction Equation A with the fluorine-containing alcohol (III) is conducted in the presence or absence of a catalyst usually in an organic solvent which is inert to the isocyanate group. Examples of useful organic solvents are 1,1,1-trichloroethane, trichloroethylene, trichloromethane, trichlorotrifluoroethane and like halogenated hydrocarbons; benzene, toluene, and like aromatic hydrocarbons; hexane, heptane and like saturated hydrocarbons; ethylene glycol dimethyl ether, ethylene glycol diethyl ether, diethylene glycol dimethyl ether and like ethers; acetone, methyl ethyl ketone, methyl isobutyl ketone and like ketones; etc. Among them, it is preferred to use those capable of dissolving water such as ethers and ketones to smoothly react the solvent with the water in Equation B. Useful catalysts include a wide variety of those to be commonly used in the reaction for synthesis of urethane or polyurethane (i.e., reaction between isocyanate and hydroxyl). Illustrative of such catalysts are triethylamine, triethylenediamine, stannous octylate, etc. The amount of the catalyst is about 0.5 to about 5 mole % to that of the compound (II) or (VI). The ratio between the compound (II) or (VI) and the compound (III) is not particularly limited. The amount of the compound (III) is usually about 0.5 to about 5.0 moles, preferably about 1.0 to about 3.0 moles, per mole of the compound (II). The amount of the compound (III) is in the range of usually about 0.8 to about 1.2 moles, preferably about 1 mole, per mole of the compound (VI). The reaction is usually carried out at a temperature in the range from 25 to 100° C., preferably from 40° to 100° C., and is completed usually in about 1 to about 3 hours. To preclude a side reaction, the reaction is preferably effected in the absence of water.

After completing the reaction of Equation (1), the reaction of Equation (2) between the compound (IV) and the lower alcohol (V) is performed preferably under the same conditions as the reaction of Equation A without separating the compound (IV) from the reaction mixture. Usually the reaction of Equation (2) is initiated by merely adding a predetermined amount of the lower alcohol (V) to the reaction mixture subsequent to the reaction of Equation (1). Alternatively the compound (IV) or (VII) isolated from the reaction mixture can be used to react with the alcohol (V) or water. The amount of the alcohol (V) ranges ordinarily from about 0.5 to about 5.0 moles, preferably from about 1.0 about 3.0 moles, per mole of the compound (IV). The reaction is completed usually in about 2 to about 5 hours.

The reaction of Equation B between the compound (VII) and water is effected desirably under conditions similar to those in Equation A without isolating the compound (VII) from the reaction mixture resulting from the reaction of Equation A. Ordinarily a predetermined amount of water is added to the reaction mixture to start the reaction of Equation B. Alternatively the compound (VII) separated from the reaction mixture can be added to water. The amount of water is usually about 0.4 to about 0.6 mole, preferably 0.5 mole, per mole of the compound (VII). The reaction time is ordinarily about 2 to about 5 hours.

In this reaction, 1 mole of the compound (VII) is reacted with 1 mole of water to provide 1 mole of an amino compound (VIII) which is then reacted with 1 mole of the compound (VII) remaining in the reaction system, whereby the compound (I') of the present invention is produced as shown in Equation B.

The compound of the invention can be utilized in the form of organic solvent solution or aqueous emulsion for various uses. It is particularly useful as an oil and water-repelling agent and a non-sticking agent because of the presence of a perfluoroalkyl group having a low surface energy as the side chain.

An oil and water-repelling agent is a substance which gives a property of repelling aqueous and oily substances to the surface of a solid substrate due to decreasing in the critical surface tension of said surface. The aqueous substances include water and aqueous solutions of water-soluble materials such as alcohols. The oily substances include mineral, animal and vegetable oils and fats such as lamp oil, heavy oil, gasoline, liquid paraffin, pitch, asphalt, cotton oil, rape oil and whale oil.

A non-sticking agent is a substance which prevents adhesion of adhesive materials to substrate a by decreasing the critical surface tension of the surface of said substrate. It comprises a releasing agent, a releasing sheet-processing agent, a backing agent, an anti-blocking agent, etc. The releasing agent is usually applied to a metal or wooden mold in a molding process for rubber, synthetic resin or the like by spraying or coating in order to assure good releasing. Sometimes, it is incorporated into a rubber or synthetic resin composition so as to impart thereto a self-releasing property. The backing agent is used, for instance, for backing a pressure sensitive adhesive tape to prevent its adhesion and facilitate its releasing. The releasing sheet processing agent is employed for production of a releasing sheet or paper to be used in a molding process of film, plate, etc. The anti-blocking agent is used as a treating agent for prevention of blocking between sheets, film, etc. kept in a closely contacted state for a long duration of time.

For practical use as the oil and water-repelling agent or the non-sticking agent, the compound of the invention may be dissolved in an organic solvent (e.g. acetone, methyl ethyl ketone, ethyl acetate, dimethylformamide, methyl chloroform, trichloroethylene, trichlorotrifluoroethane, tetrafluorodifluoroethane) to make a solution. Alternatively, a solution of the compound of the invention obtained by solution polymerization may be diluted with such a solvent as mentioned above. The thus prepared solution or dilution may be incorporated with a propellant such as dichlorodifluoromethane, monofluorotrifluoromethane, dimethyl ether, etc. and charged into an appropriate container to make an aerosol. Further, the compound of the invention may be dispersed into an aqueous medium together with various additives in the presence of a suitable surfactant as an emulsifier to make an aqueous emulsion. As the surfactant, any anionic, nonionic and cationic surfactant can be utilized without particular limitation. In some cases, the compound of the invention may be as such applied to a substrate by any suitable procedure.

The oil and water-repelling agent containing the compound of the invention can be applied to various substrates without particular limitation. For example, textile fabrics and paper are treated with particular advantage. There may be also exemplified porous materials such as wood, leather, fur, felt, asbestos and brick, and materials having a smooth surface such as metal, tile, plastics and various coated surfaces. Textile fabrics comprise the ones made from natural fibers of animal and plant origins (e.g. cotton, flax, wood, silk), synthetic fibers (e.g. polyamide, polyester, polyvinyl acetal, polyacrylonitrile, polyvinyl chloride, polypropylene), hemisynthetic fibers (e.g. rayon, acetate fiber), inorganic fibers (e.g. glass fiber, asbestos fiber) and their mixed fiber.

The non-sticking agent containing the compound of the invention as the active ingredient can be also applied to almost all of the substrates as mentioned above. The adhesive materials as the target of the non-sticking agent of the invention are natural or synthetic resins or rubbers such as polyurethane resin, epoxy resin, phenol resin, vinyl chloride resin, acryl resin, natural rubber, chloroprene rubber and fluorine-containing rubber. Industrially, the non-sticking agent is applicable, as a so-called "releasing agent", to a metal mold, a wooden mold, a plastic mold and a paper mold in molding of plastics and rubber, or applicable for backing of adhesive tape made of paper, cellophane, cloth, plastic film or metal foil, or as backing agent for a releasing paper for adhesive-backed labels, seals, stickers, etc.

The concentration of the compound in the oil and water-repelling agent is not particularly limited. Usually, a concentration of about 0.01 to about 30% by weight, preferably about 0.1 to about 2.0% by weight, may be adopted. With a solution having too low a concentration, the oil and water-repelling property is not given sufficiently. Too high a concentration is disadvantageous from the economical viewpoint.

The procedure for application of the oil and water-repelling agent or the non-sticking agent containing the compound of the invention as the active ingredient to a substrate may be appropriately selected depending on their preparation forms, the kind of the substrate, the purpose of the use of the substrate, etc. When, for example, formulated in a solution or an aqueous emulsion, it may be applied to the surface of the substrate by a conventional procedure such as spraying, immersion or coating, followed by drying, and if necessary, curing. An aerosol may be sprayed over the substrate and then dried.

The oil and water-repelling agent of the invention may contain, in case of necessity, various additives such as an anti-static agent, a fire-proofing agent and a sizing agent. Further, film forming resins such as acryl resins and vinyl acetate resins or fine powders of silicon oxide and polytetrafluoroethylene may be incorporated therein. The non-sticking agent of the invention may contain, in case of necessity, film forming resins such as acryl resin and vinyl acetate resin, paints such as lacquer and vinyl chloride paint, fine powders of silicon oxide and polytetrafluoroethylene, oils such as silicone oil and fluorine oil, etc.

In a water or oil repelling agent, the concentration of the present compound present is not particularly limited. Usually it is about 0.01 to about 30 wt.%, preferably about 0.1 to about 2.0 wt.%. The solution having a very low concentration of the present compound provides the articles with poor water or oil repellency and the solution having a very high concentration thereof is economically disadvantageous.

In a non-sticking agent, less than 0.1 wt.% of the present compound as contained is sufficient when the agent is used for one cycle of molding operation. When employed for a prolonged release lifetime, the non-sticking agent contains about 0.05 to about 30 wt.%, preferably about 0.1 to about 10 wt.% of the present compound. Substantially the same amount of the present compound is incorporated in a backing agent or an anti-blocking agent. When incorporated as an inner releasing agent into a resin material to be molded, about 0.05 to about 10 wt.%, preferably about 0.1 to about 3 wt.%, of the present compound is used as a mold release agent relative to the resin.

The present invention will be described below in more detail with reference to the following Examples in which the parts and percentages are all by weight unless otherwise specified.

EXAMPLE 1

A 200-cc, 4-necked flask equipped with a dropping funnel having a pressure balancing tube, a thermometer, a nitrogen tube and a magnetic stirrer was set on a silicone oil bath. In the flask were placed 3.67 g (0.01 mole) of p,p',p"-triphenylmethanetriisocyanate (C-1) and 50 g of dimethoxyethane. The mixture was stirred while forcing nitrogen into the flask through the nitrogen tube. The feed of nitrogen was ceased in 15 minutes and the nitrogen tube was replaced by a condenser and the liquid was maintained at a temperature of 70° C. A 5.14 g (0.01 mole) quantity of

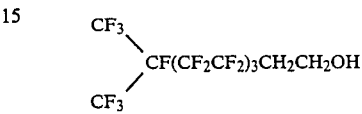

was added dropwise over 30 minutes through the dropping funnel under dry nitrogen atmosphere. After completion of the addition, the mixture was stirred for 30 minutes and was cooled to 40° C. A 0.64 g (0.02 mole) quantity of methaol was added and agitation was continued for 1 hour. The reaction mixture was withdrawn and the dimethoxyethane (solvent) was distilled off in an evaporator. Vacuum drying gave 0.3 g of a white solid, M.P. 100° C. The product was analyzed by gas chromatography, infrared absorption spectrum and elementary analysis and the contemplated compound of the formula

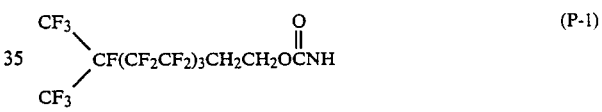

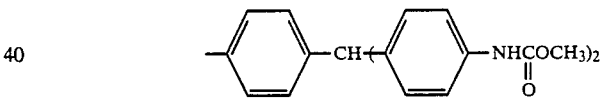

(P-1)

was found to have a selectivity of 95%.

Infrared absorption spectrum: 3330, 3050, 1708–1720, 1600, 1535, 1150–1300 cm$^{-1}$.

Elementary analysis: Calcd.: C, 44.4%; N, 4.44%; F, 38.2%. Found: C, 45.0%; N, 4.62%; F, 37.5%.

The compound was obtained in 94% yield based on the starting material, p,p',p"-triphenylmethanetriisocyanate.

EXAMPLE 2

The procedure of Example 1 was repeated by using 3.67 g (0.01 mole) of p,p',p"-triphenylmethanetriisocyanate (C-1), 9.28 g (0.02 mole) of $C_8F_{17}CH_2CH_2OH$ and 0.32 g (0.01 mole) of methanol, producing 13.0 g of the contemplated compound of the formula

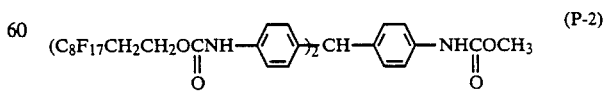

(P-2)

as a white solid melting at 121° C.

Infrared absorption spectrum: 3330, 3050, 1708–1730, 1600, 1535, 1150–1300 cm$^{-1}$.

Elementary analysis: Calcd.: C, 38.9%; N, 3.2%; F, 48.7%. Found: C, 39.5%; N, 3.5%; F, 47.5%.

The contemplated compound (P-2) was found to have a selectivity of 93% and a yield of 93% based on the starting material, p,p',p''-triphenylmethanetriisocyanate.

EXAMPLE 3

The procedure of Example 1 was repeated by usng 6.56 g (0.01 mole) of $$\text{CH}_3\text{C}(\text{CH}_2\overset{O}{\underset{\|}{\text{C}}}\text{NH}-\underset{\text{CH}_3}{\text{C}_6\text{H}_3}-\text{NCO})_3$$

(C-2), 10.28 g (0.02 mole) of $$\underset{\text{CF}_3}{\overset{\text{CF}_3}{\diagdown}}\text{CF}(\text{CF}_2\text{CF}_2)_3\text{CH}_2\text{CH}_2\text{OH}$$

and 0.32 g (0.01 mole) of methanol, producing 16.6 g of the contemplated compound of the formula (P-3)

$$\text{CH}_3\text{C}\left(\text{CH}_2\text{O}\overset{O}{\underset{\|}{\text{C}}}\text{NH}-\underset{\text{CH}_3}{\text{C}_6\text{H}_3}-\text{NH}\overset{O}{\underset{\|}{\text{C}}}\text{OCH}_2\text{CH}_2-(\text{CF}_2\text{CF}_2)_3\text{CF}(\text{CF}_3)_2\right)_?$$

(with NHCOCH$_3$ group shown on ring)

as a white solid melting at 112° C.

Infrared absorption spectrum: 3330, 2980, 1725, 1600, 1540, 1150–1300 cm$^{-1}$.

Elementary analysis Calcd.: C, 38.5%; N, 4.9%; F, 42.1%. Found: C, 39.2%; N, 5.1%; F, 41.5%.

The contemplated compound (P-3) was found to have a selectivity of 97% and a yield of 93% based on the starting material, isocyanate.

EXAMPLE 4

The procedure of Example 1 was followed by using 5.22 g (0.01 mole) of a compound of the formula (C-3)

[isocyanurate ring with three tolyl-NCO substituents]

5.8 g g (0.01 mole) of $$\text{C}_8\text{F}_{17}\text{SO}_2\overset{\text{C}_3\text{H}_7}{\underset{|}{\text{N}}}\text{CH}_2\text{CH}_2\text{OH}$$

and 0.64 g (0.02 mole) of methanol, producing 11.5 g of the contemplated compound of the formula (P-4)

[isocyanurate with three aryl groups: two bearing NHCOOCH$_3$/CH$_3$ and one bearing NHCCH$_2$CH$_2$N(C$_3$H$_7$)SO$_2$C$_8$F$_{17}$, and one bearing NHCOCH$_3$/CH$_3$]

as a white solid melting at 140° C.

Infrared absorption spectrum: 3360, 2980, 1705–1725, 1600, 1540, 1415, 1200–1280 cm$^{-1}$.

Elementary analysis Calcd.: C, 42.0%; N, 8.4%; F, 27.6%. Found: C, 42.5%; N, 8.0%; F, 26.9%.

The contemplated compound (P-4) was found to have a selectivity of 95% and a yield of 92% based on the starting compound, isocyanate (C-3).

EXAMPLE 5

The procedure of Example 1 was repeated by using 3.07 g (0.01 mole) of p,p',p''-triphenylmethanetriisocyanate (C-1) and 16.9 g (0.03 mole) of $$\underset{\text{CF}_3}{\overset{\text{CF}_3}{\diagdown}}\text{CF}(\text{CF}_2\text{CF}_2)_n\text{CH}_2\text{CH}_2\text{OH}$$

(n=3.5), producing 19.9 g of the contemplated compound of the formula (P-5)

$$\text{CH}\left(\!\!\!\raisebox{-2pt}{\text{—}}\!\!\!\bigcirc\!\!\!\raisebox{-2pt}{\text{—}}\!\!\!\text{NH}\overset{O}{\underset{\|}{\text{C}}}\text{OCH}_2\text{CH}_2(\text{CF}_2\text{CF}_2)_{3.5}\text{CF}(\text{CF}_3)_2\right)_3$$

as a white solid melting at 101° C.

The contemplated compound (P-5) was found to have a selectivity of 99% and a yield of 97% based on the starting material, isocyanate.

EXAMPLE 6

The procedure of Example 1 was repeated by using 3.67 g (0.01 mole) of p,p',p"-triphenylmethanetriisocyanate (C-1), and 11.3 g (0.02 mole) of

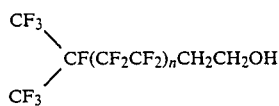

(n=3.5), and 0.6 g (0.01 mole) of $CH_3CH_2CH_2OH$, producing 15.4 g of the contemplated compound of the formula

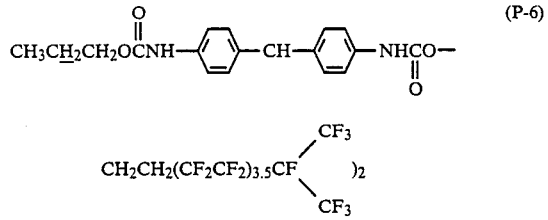

(P-6)

as a white solid melting at 75° to 78° C.

The contemplated compound (P-6) was found to have a selectivity of 95% and a yield of 93% based on the starting material, isocyanate.

EXAMPLE 7

The compound (P-1) obtained in Example 1 was dissolved in a concentration of 1% in a 1:1 volume ratio mixture of trichlorotrifluoroethane and acetone. A piece of cotton/polyester (35/65) blended fabric was immersed in the solution, squeezed by a mangle to a liquid take-up of 100% and dried at 100° C. for 3 minutes. By using the fabric thus treated, the water repellency and oil repellency of the compound (P-1) were measured and evaluated as 100 and 6, respectively.

The oil and water-repelling property in these Examples is evaluated by the following criterion: the water-repelling property being indicated by the water-repellency number determined by the spray method according to JIS L-1005; the oil-repelling property being indicated by the oil-repellency number determined by dropping a different n-alkane having a different surface tension onto a specimen and observing whether the drop is kept or not for 3 minutes or more according to AATCC 118-1972.

EXAMPLE 8

The compounds (P-2), (P-3) and (P-4) prepared in Examples 2, 3 and 4, respectively were also subjected to water and oil repellency tests in the same manner as in Example 7, using a piece of cotton/polyester (35/65) blended fabric. Table 1 below shows the results.

TABLE 1

| Compound | Water Repellency | Oil Repellency |
|---|---|---|
| (P-2) | 100 | 7 |
| (P-3) | 100 | 7 |
| (P-4) | 100 | 6 |

EXAMPLE 9

A portion of the compound (P-5) obtained in Example 5 was dissolved in a concentration of 0.8 wt.% in a 1:1 volume ratio mixture of trichlorotrifluoroethane and acetone. An aerosol container was filled with 350 parts of the solution and 100 parts of dichlorodifluoromethane to produce an aerosol. The aerosol was sprayed over a polyester-napped fabric to be used for an electric carpet to an extent sufficient to render the entire portion of sprayed fabric slightly wet. The fabric was dried at room temperature for 30 minutes. Droplets of a 30:70 volume ratio isopropyl alcohol water mixture were deposited on the fabric and were found to remain thereon for over 3 minutes. The compound was also tested for oil repellency and rated as 7.

EXAMPLE 10

A 1 part portion of the compound (P-5) obtained in Example 5 was dissolved in 99 parts of trichlorotrifluoroethane. The solution was applied to a steel mold and air-dried. The mold had a cavity having a diameter of 40 mm and a depth of 2 mm for disc molding. For comparative purpose, commercial mold release agents α (silicone type) and β (oil and fat wax type) were each diluted to a concentration of 1% with toluene and each brush-coated to the same type of steel molds. A 100-part portion of Epikote #828 (curing-type epoxy resin, product of Shell Kagaku Kabushiki Kaisha, Japan) and 10 parts of triethylenetetramine were mixed well and placed in each of the three steel molds, followed by being allowed to stand for 2 hours at a normal temperature and heating at 100° C. for 1 hour. A pin was put in the central portion of the cavity in each mold to facilitate the removal of molded articles after hardening. Then, the pin was pulled to remove the resulting molded articles from the mold, whereupon the release ability was determined by the pulling impression according to the following standard.

Release Ability Determination Standard
  5: Molded article is removed from the mold by extremely slight pulling force.
  4: Removed by slight pulling force.
  3: Removed by moderate pulling force.
  2: Hard to be removed by fair pulling force.
  1: Molded article is adhered to the mold and can not be removed by hand pulling.

This release test revealed that the compound (P-5) had a release ability of 5, whereas the mold release agents α and β both exhibited 2.

EXAMPLE 11

A 500-cc, 4-necked flask equipped with a dropping funnel having a pressure balancing tube, a thermometer, a nitrogen tube and a magnetic stirrer was set on a silicone oil bath. In the flask were placed 17.4 g (0.1 mole) of 2,4-tolylenediisocyanate and 200 g of methyl ethyl ketone and the mixture was stirred while forcing nitrogen into the flask through the nitrogen tube. The feeding of nitrogen was stopped in 15 minutes and the nitrogen tube was replaced with a condenser. The liquid was maintained at a temperature of 75° C. Under dry nitrogen atmosphere, 51.4 g (0.1 mole) of

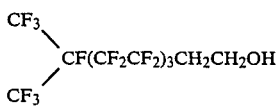

was added dropwise by the dropping funnel over 45 minutes. After completion of the addition, the mixture was stirred for 30 minutes. A 0.9 g (0.05 mole) quantity of water was added and agitation was continued for 3 hours. The reaction mixture was withdrawn and the methyl ethyl ketone (solvent) was distilled off by an evaporator. Vacuum drying gave 64 g of a white solid melting at 85° C. The solid was analyzed by gas chromatography and infrared absorption spectrum and the contemplated compound of the formula

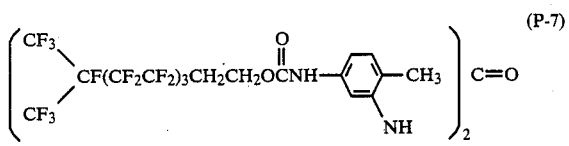
(P-7)

was found to be obtained in a selectivity of 98% and a yield of 95% based on the starting material, 2,4-tolylenediisocyanate.

EXAMPLE 12

The procedure of Example 11 was repeated by using 25 g (0.1 mole) of 4,4'-diphenylmethanediisocyanate and 51.4 g (0.1 mole) of

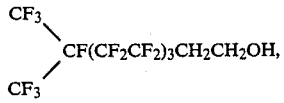

producing 70 g of the contemplated compound of the formula

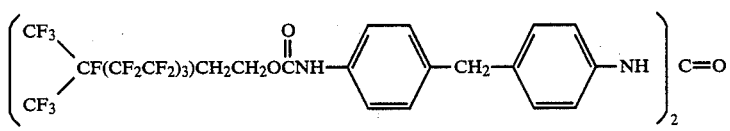
(P-8)

as a white solid melting at 90° to 91° C.

The compound (P-8) was found to be obtained in a selectivity of 97% and a yield of 96% based on the starting material, 4,4'-diphenylmethanediisocyanate.

EXAMPLE 13

The procedure of Example 11 was repeated by using 18.8 g of xylylenediisocyanate and 58.5 g of

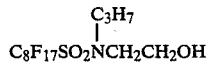

in ethylene glycol dimethyl ether, producing 69 g of the contemplated compound of the formula

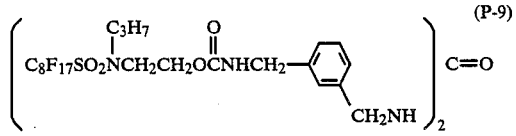
(P-9)

The compound (P-9) was found to be obtained in a selectivity of 95% and a yield of 93% based on the starting material, xylylenediisocyanate.

EXAMPLE 14

Using 26.2 g of 4,4'-dicyclohexylmethanediisocyanate and 46.4 g of $C_8F_{17}CH_2CH_2OH$, the procedure of Example 11 was repeated, giving 65 g of the contemplated compound of the formula

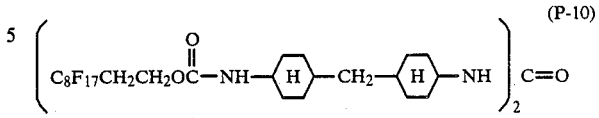
(P-10)

The compound (P-10) was found to be obtained in a selectivity of 96% and a yield of 94% based on the starting material, 4,4'-dicyclohexylmethanediisocyanate.

EXAMPLE 15

A portion of the compound (P-7) obtained in Example 11 was dissolved in a concentration of 1 wt.% in a 1:1 volume ratio mixture of trichlorotrifluoroethane and acetone. A piece of cotton/polyester (35/65) blended fabric was immersed in the solution. The fabric was squeezed by a mangle to a liquid take-up of 100% and dried for 3 minutes at 100° C. The fabric thus treated was subjected to water and oil repellency tests. As a result, the compound (P-7) was found to have a water repellency of 100 and an oil repellency of 6.

EXAMPLE 16

A portion of the compound (P-8) was dissolved in a concentration of 0.8 wt.% in a 1:1 volume ratio mixture of trichlorotrifluoroethane and acetone. A 350 part portion of the solution and 100 parts of dichlorodifluoromethane were charged into an aerosol container to produce an aerosol. The aerosol was sprayed over a polyester-napped fabric to be used for electric carpets to such extent that the whole sprayed portion of the fabric was rendered slightly wet. The fabric was dried at room temperature for 30 minutes. Droplets of a 30:70 volume ratio isopropyl alcohol-water mixture were deposited on the fabric, and the deposited droplets were found to remain for over 3 minutes. The oil repellency of the compound was 7.

EXAMPLE 17

A 1 part portion of the compound (P-10) obtained in Example 14 was dissolved in a mixture of 90 parts of trichlorotrifluoroethane and 9 parts of acetone. The solution was applied by brushing to a steel mold and air-dried. The mold had a cavity having a diameter of 40 mm and a depth of 2 mm for disc molding. For comparative purpose, commercial mold release agents A (silicone type) and B (oil and fat wax type) were each diluted to a concentration of 1% with toluene and brush-coated to the same type of steel molds. Epikote #828 (curing-type epoxy resin, product of Shell Kagaku Kabushiki Kaisha, Japan) and 10 parts of triethylenetetramine were mixed well and placed in the molds, followed by being allowed to stand for 2 hours at a normal temperature and heating at 100° C. for 1 hour. A pin was put in the central portion of the cavity to facilitate the removal of molded articles after hardening. The pin was pulled to remove the molded articles from the mold, whereupon the release ability was determined by the pulling impression according to the standard mentioned hereinbefore in Example 10.

As a result, the compound (P-10) was found to have a release ability of 5, whereas the mold release agents A and B were both rated as 2.

We claim:

1. A fluorine-containing urethane compound represented by the formula

wherein $R_f$ is a perfluoroalkyl group having 4 to 20 carbon atoms; X is $-C_kH_{2k}$, wherein k is an integer of 1 to 4; and $R^1$ is a trivalent organic group represented by the formula

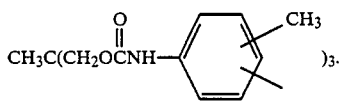

2. A fluorine-containing urethane compound represented by the formula

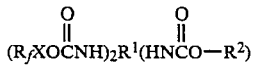

wherein $R_f$ is a perfluoroalkyl group having 4 to 20 carbon atoms; X is $-C_2H_{2k}$, wherein k is an integer of 1 to 4; $R^1$ is a trivalent organic group represented by the formula

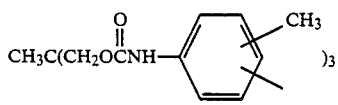

and $R^2$ is an alkyl having 1 to 5 carbon atoms.

3. A fluorine-containing urethane compound represented by the formula

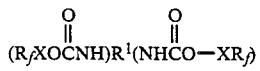

(I)

wherein $R_f$ represents a perfluoroalkyl group having 4 to 20 carbon atoms; X represents $-C_kH_{2k}-$ or $SO_2N(R^3)C_tH_{2t}-$, in which each of k and t is an integer of 1 to 4; and $R^3$ is hydrogen or an alkyl having 1 or 2 carbon atoms; and $R^1$ is a divalent organic group represented by the formula

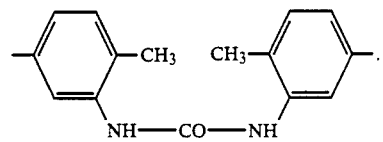

4. A fluorine-containing urethane compound represented by the formula

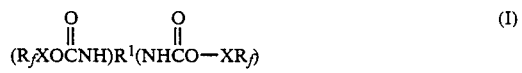

(I)

wherein $R_f$ represents a perfluoroalkyl group having 4 to 20 carbon atoms; X represents $-C_kH_{2k}-$ or $SO_2N(R^3)C_tH_{2t}-$, in which each of k and t is an integer of 1 to 4; and $R^3$ is hydrogen or an alkyl having 1 or 2 carbon atoms; and $R^1$ is a divalent organic group represented by the formula

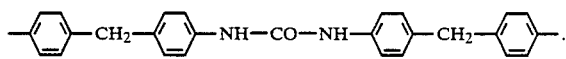

5. A fluorine-containing urethane compound represented by the formula

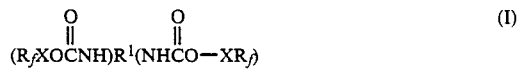

(I)

wherein $R_f$ represents a perfluoroalkyl group having 4 to 20 carbon atoms; X represents $-C_kH_{2k}-$ or $SO_2N(R^3)C_tH^{2t}-$, in which each of k and t is an integer of 1 to 4; and $R^3$ is hydrogen or an alkyl having 1 or 2 carbon atoms; and $R^1$ is a divalent organic group represented by the formula

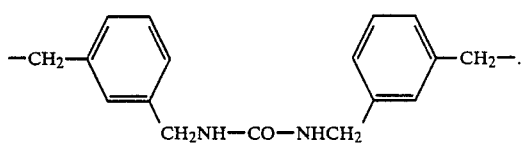

6. A fluorine-containing urethane compound represented by the formula

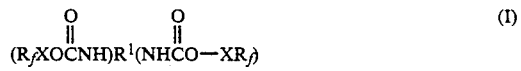

(I)

wherein $R_f$ represents a perfluoroalkyl group having 4 to 20 carbon atoms; X represents $-C_kH_{2k}-$ or $SO_2N(R^3)C_tH_{2t}-$, in which each of k and t is an integer of 1 to 4; and $R^3$ is hydrogen or an alkyl having 1 or 2 carbon atoms; and $R^1$ is a divalent organic group represented by the formula

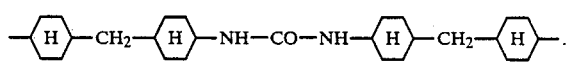

* * * * *